Figure 1:
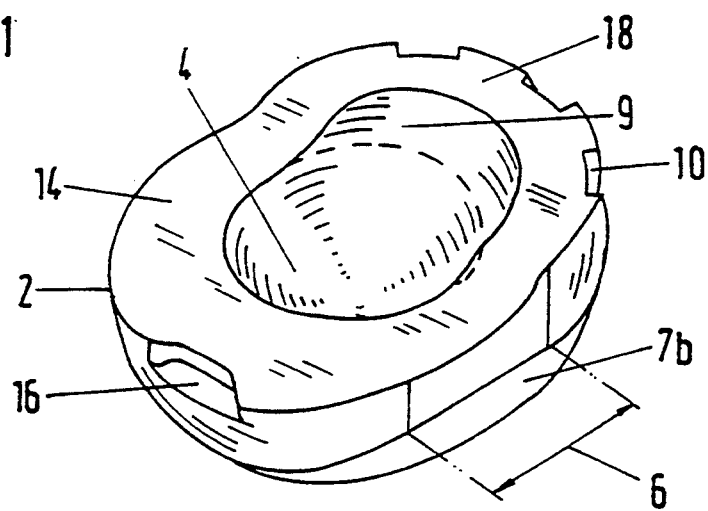

United States Patent [19]
Willert et al.

[11] Patent Number: 5,370,703
[45] Date of Patent: Dec. 6, 1994

[54] DOUBLE-CUP HIPJOINT SOCKET SUITABLE FOR USE IN REVISION

[75] Inventors: Hans-Georg Willert, Göttingen, Germany; Rudolf Koch, Frauenfeld; Kurt Bider, Winterthur, both of Switzerland

[73] Assignees: Sulzer Medizinaltechnik AG, Winterthur; Allo Pro AG, Baar, both of Switzerland

[21] Appl. No.: 113,937
[22] Filed: Aug. 30, 1993

[30] Foreign Application Priority Data

Sep. 1, 1992 [EP] European Pat. Off. ........ 92810668.1

[51] Int. Cl.$^5$ ............................................... A61F 2/32
[52] U.S. Cl. .................................... 623/22; 623/18
[58] Field of Search ...................... 623/18, 22, 23

[56] References Cited

U.S. PATENT DOCUMENTS

| 3,584,318 | 6/1971 | Scales et al. | 623/22 |
| 5,192,329 | 3/1993 | Christie et al. | 623/22 |

FOREIGN PATENT DOCUMENTS

| 0091315 | 10/1983 | European Pat. Off. . |
| 0245527 | 11/1987 | European Pat. Off. . |
| 0303006 | 2/1989 | European Pat. Off. . |
| 0313762 | 5/1989 | European Pat. Off. . |
| 0341199 | 11/1989 | European Pat. Off. . |
| 0482320 | 4/1992 | European Pat. Off. ...... 623/22 |
| 2617040 | 12/1988 | France . |

*Primary Examiner*—David Isabella
*Attorney, Agent, or Firm*—Townsend and Townsend Khourie and Crew

[57] ABSTRACT

The invention shows a double-cup hipjoint socket of oval cross-section with a spherical bearing cup (4). the metallic outer cup (1) exhibits a constant thickness of wall and is provided with openings (3) for anchoring in the pelvic bone. The inner cup (2) of plastics may be latched to the outer cup (1) and by springy tongues (11) on the opposite side. The oval shape is generated by inserting straight intermediate pieces (5,6) in the inner and outer cups. Through the elongated shape of the outer cup (1) which may be inserted in different directions, an optimum fastening may be striven for. The definitive position of the spherical bearing cup (4) is established for the first time by the insertion of a fitting inner cup (2). In doing so the spherical bearing cups (4) may be shifted in the equatorial plane of the outer cup (1) and/or in the direction of the polar axis of the outer cup.

5 Claims, 2 Drawing Sheets

DOUBLE-CUP HIPJOINT SOCKET SUITABLE FOR USE IN REVISION

The invention deals with a double-cup hipjoint socket suitable for use in revision, consisting of a metal outer cup which may be anchored in the pelvic bone by bone screws through openings, and of an inner cup which may be inserted intraoperatively and exhibits a spherical bearing-cup for a ball head and snaps into the outer cup by a snap connection.

A double-cup hipjoint socket with a snap-in connection is shown in the EP 0 313 762. Revision, i.e., the replacement of a hipjoint socket is practically always connected with a loss of substance in the bone of the pelvis. The operating surgeon must rework the bed in the bone and necessarily arrives at a bearing area which is offset into the bone and claims a greater volume. At the same time the spherical bearing cup for the ball egad, with optimum anchoring of the outer cup, should preserve its ideal position for the ball head. The invention takes this circumstance into account. The problem it faces is to give the operating surgeon more freedom for the fastening of the outer cup without imparing the conditions at the spherical bearing cup for receiving a ball head.

This problem is solved by the present invention. The advantages of the invention are to be seen in that by the oval shape of the outer cup a connection to the pelvic bone is achieved which is secure against rotation and by the oval shape of the inner cup a connection to the outer cup which is secure against rotation and allows tilting moments to be withstood, such as arise when the centre of the spherical bearing cup is offset towards the outside from the centre of the outer cup.

Through the employment of an inner cup of plastics, a damping action arises against impact loadings. The plastics further allows inner cups to be worked beforehand as regards their fastenings to the outer cup and stored as semimanufactures in order to finish them at short notice for extreme positions of the spherical bearing area. The straight intermediate pieces at the circumference and the clear bearing areas facilitate the gripping and finishing of the semimanufactures.

Figure 2:
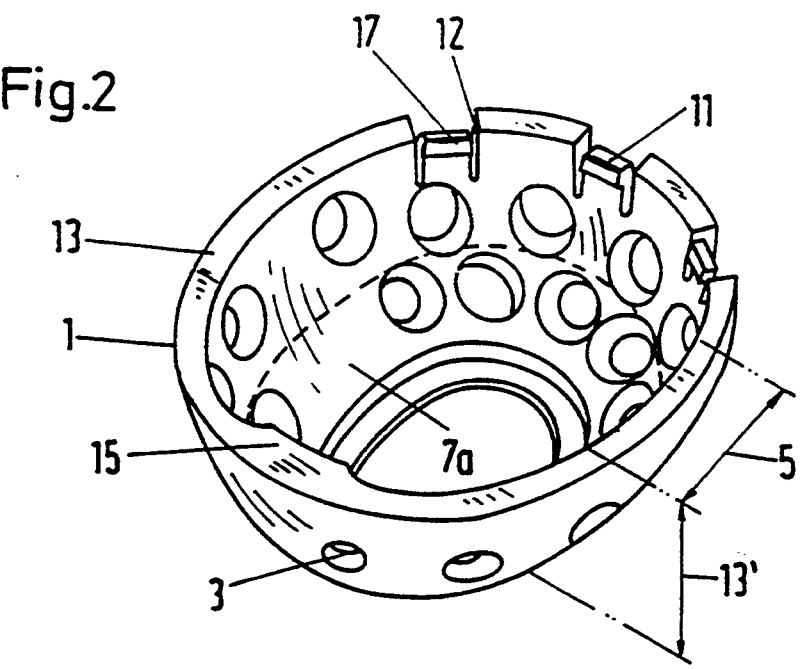
Figure 3:
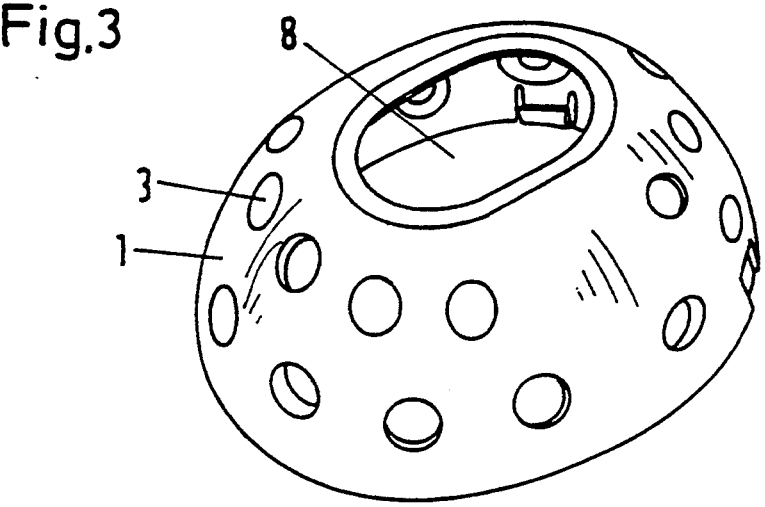

The invention is described below with the aid of embodiments There is shown diagrammatically in:

FIG. 1—a view of a finished inner cup with a spherical bearing cup and an elevated edge at one side;

FIG. 2—a view of the inside of an outer cup;

FIG. 3—a view of the outside of an outer cup; and

Figure 4:
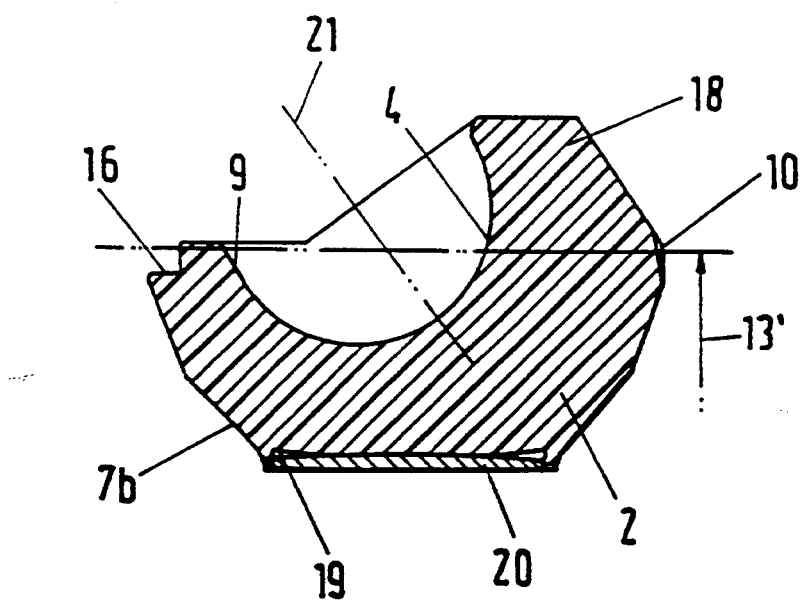

FIG. 4—the longitudinal section through an inner cup which exhibits a spherical bearing cup with a pronounced lateral offset.

In the Figures a double-cup hipjoint socket is shown, which is of oval cross-section with a spherical bearing cup 4. The metallic outer cup 1 exhibits a constant wall thickness and is provided with openings 3 for anchoring in the pelvic bone. The inner plastic cup 2 may be latched to the outer cup 1 by swinging about a lug 15 on the equator of the outer cup 1 and by springy tongues 11 on the opposite side. The oval shape is generated by inserting straight intermediate pieces 5, 6 in the inner and outer cups. Through the elongated shape of the outer cup 1 which may be inserted in different directions, an optimum fastening may be striven for. The definitive position of the spherical bearing cup 4 is established for the first time by the insertion of a fitting inner cup 2. In doing so, the spherical bearing cups 4 may be shifted in the equatorial plane of the outer cup 1 and/or in the direction of the polar axis of the outer cup.

FIG. 1 shows the inner cup 2 and FIG. 2 shows the receiving outer cup 1 of the hipjoint socket.

With straight intermediate pieces 6 or 5, respectively inserted, the inner cup 2 and outer cup 1 exhibit in cross-section an oval shape. This oval shape is also continued in the bearing areas between the outer cup and inner cup, which consist of oblique peripheral areas 7a and 7b respectively and exhibit straight generatrices. The oblique areas 7a, 7b are pressed together by the inner cup 2 being mounted with a recess 16 against a lug 15 on the equator of the outer cup and swung about the said lug transversely to the longitudinal axis until a snap connection 17 snaps onto the opposite edge of the equator. The snap connection 17 is performed by springy tongues 11 which are created through slits 12 in the wall of the outer cup. The tongues 11 exhibiting oblique run-up faces projecting into the interior, by which the tongues 11 may be prestressed during swinging in the inner cup until they can snap home, upon the oblique areas 7a, 7b coming into contact with one another.

FIG. 3 shows in the polar region of the outer cup 1 a likewise oval opening 8 which during fastening of the outer cup serves as a checking opening and allows plugging with bone chips. The actual fastening of the outer cup 1 is done by bone screws (not shown here) which rest with their heads in countersunk openings 3 in order not to impede the mutual centreing of the oblique areas 7a, 7b. The openings 3 are moreover distributed mainly on the round regions of the outer cup 1 at different heights and allow secure fastening also in the caudal region in order to absorb moments via the middle region with the straight intermediate piece 5 acting as a lever arm.

With the outer cup 1 already fastened, inner cups 2 may be inserted in it, having different positions of the spherical bearing cup 4 with respect to the outer cup 1. Again, the radius of the spherical bearing cup may vary. Through the oval shape of the outer cup 1, the spherical bearing cups 4 may adopt quite different positions with respect to the outer cup 1. Thus, FIG. 1 shows an inner cup 2 the spherical bearing cup 4 of which terminates at the edge of the outer cup and against which an elevation 18 with a cylindrical guideface 9 is mounted in order to prevent luxations of an inserted joint ball.

FIG. 4 shows a heavily lateralized position of the spherical bearing cup 4. The centre of the radius of the spherical bearing cup 4 lies far outside the height 13' of the edge of the outer cup 1 and its polar axis 21 is lying obliquely to the equator of the outer cup 1. In that case the polar axis 21 is inclined to such an extent that inside the height 13' of the edge of the outer cup a cylindrical guideface 9 arises.

On the underside the inner cup 2 of FIG. 4 has an oval recess 19 into which a metal plate preferably of titanium is pressed. By the insertion of the inner cup 2, the plastics of the inner cup 2 in the region of the opening 8 is covered by metal with respect to the bed in the bone.

We claim:

1. A double-cup hipjoint socket suitable for revision comprising:
   a metal outer cup having a plurality of openings sized to accommodate bone screws for connecting the outer cup to a pelvic bone, the outer cup having a constant wall thickness;

a plastic inner cup sized to fit within the outer cup and having a spherical bearing cup for a joint ball head, the inner and outer cups having opposing oblique peripheral faces with straight generatrices;

the inner and outer cups including first and second substantially straight intermediate sections giving each cup an oval cross-section; and connection means for fixing the inner cup to the outer cup, the connection means including a lug and at least two spring tongues on the outer cup, the inner cup being adapted to fit within the lug and rotate transversely to the longitudinal axis of the outer cup, the spring tongues latching the inner cup so that the inner cup and outer cup are pressed together at the opposing oblique peripheral faces.

2. The hipjoint socket of claim 1 wherein the outer cup has an oval opening at a polar region of the cup.

3. The hipjoint socket of claim 1 wherein the spherical bearing cup has a given diameter and a given angle with respect to a polar angle of the outer cup, the outer cup being adapted to accommodate a different spherical bearing cup, the different spherical bearing cup having a diameter that is not equal to the given diameter of the spherical bearing cup and an angle with respect to the polar angle that is not equal to the given angle of the spherical bearing cup.

4. The hipjoint socket of claim 1 wherein the inner cup has an equatorial edge, the hipjoint socket further including an elevation formed along a portion of the equatorial edge of the inner cup, the elevation having an inner cylindrical guideface sized to prevent luxations of the joint ball head inserted into the bearing cup.

5. The hipjoint socket of claim 1 wherein the spherical bearing cup has a first equatorial edge and the outer cup has a second equatorial edge, the first edge projecting above the second edge.

* * * * *